United States Patent [19]

Brooks et al.

[11] Patent Number: 4,948,479
[45] Date of Patent: Aug. 14, 1990

[54] REMOVAL OF UNSATURATED CARBON COMPOUNDS FROM 1,1-DICHLORO-1-FLUOROETHANE

[75] Inventors: Wayne E. Brooks, Reidland; William L. Baggett, Paducah, both of Ky.

[73] Assignee: Atochem North America, Inc., Philadelphia, Pa.

[21] Appl. No.: 362,730

[22] Filed: Jun. 7, 1989

[51] Int. Cl.$^5$ .............................................. B01J 19/08
[52] U.S. Cl. ............................ 204/158.21; 204/157.94
[58] Field of Search ..................... 204/157.94, 157.95, 204/157.96, 157.97, 158.12, 158.21

[56] References Cited

U.S. PATENT DOCUMENTS

| | | | |
|---|---|---|---|
| 2,399,641 | 5/1946 | Kirkbride | 204/158.21 |
| 2,440,731 | 5/1948 | Vining et al. | |
| 2,707,197 | 4/1955 | Souillard | 204/158.21 |
| 2,945,796 | 7/1960 | Saller | 204/158.21 |
| 3,629,085 | 12/1971 | Coppens | 204/158.21 |
| 3,691,240 | 9/1972 | Kircher, Jr. et al. | |

FOREIGN PATENT DOCUMENTS

| | | | |
|---|---|---|---|
| 47-1448 | 1/1972 | Japan | 204/157.94 |
| 577241 | 5/1946 | United Kingdom | |
| 591780 | 8/1947 | United Kingdom | |

OTHER PUBLICATIONS

Chem. Abstracts, 51:16111h (1957) abstracting Ackerman et al., Bull. Soc. Chim. Belges 66, 325–344, (1957).
Chem. Abstracts 53:13748d (1959) abstracting Adam et al., Bull. Soc. Chim. Belges 65, 942–956, (1956).
Chem. Abstracts 53:17646 (1959) abstracting Chiltz et al., Bull. Soc. Chim. Belges 68, 5–18, (1959).
Chem. Abstracts 54:5461c, (1960), abstracting German Patent No. 967,011.
Dainton et al., Trans. Faraday Soc., 53, 460–467, (1957).
Dusoleil et al., Trans. Faraday Soc., 57, 2197–2209, (1961).
Huybrechts et al., Trans. Faraday Soc., 58, 1128–1136, (1962).
Huybrechts et al., Trans. Faraday Soc., 61, (513, pt. 9), 1921–1932, (1965).
Ledakowicz et al., Int. J. Chem. Kinet., 16(4), 345–352, (1984).
Anderson, Ind. Eng. Chem., 39, 844–846, (1974).
Ayscough et al., Trans. Faraday Soc., 62(7), 1838–1845 1846–1858, (1966).
Ayscough et al., Trans. Faraday Soc., 58, 284–294, (1962).
Poutsara et al., J. Am. Chem. Soc., 86(18), 3807–3814, (1964).
Beadle et al., J. Chem. Soc., Faraday Trans., 1, 70(8), 1418–1433, (1974).

Primary Examiner—John F. Niebling
Assistant Examiner—Ben C. Hsing
Attorney, Agent, or Firm—Seidel, Gonda, Lavorgna & Monaco

[57] ABSTRACT

Liquid 1,1-dichloro-1-fluoroethane containing contaminating unsaturated carbon compounds is treated with chlorine and ultraviolet light to convert the unsaturated contaminants to photochlorination products. The photochlorination products are thereafter separated from 1,1-dichloro-1-fluoroethane, such as by distillation. The process is particularly useful in separating vinylidene chloride from 1,1-dichloro-1-fluoroethane.

13 Claims, 1 Drawing Sheet

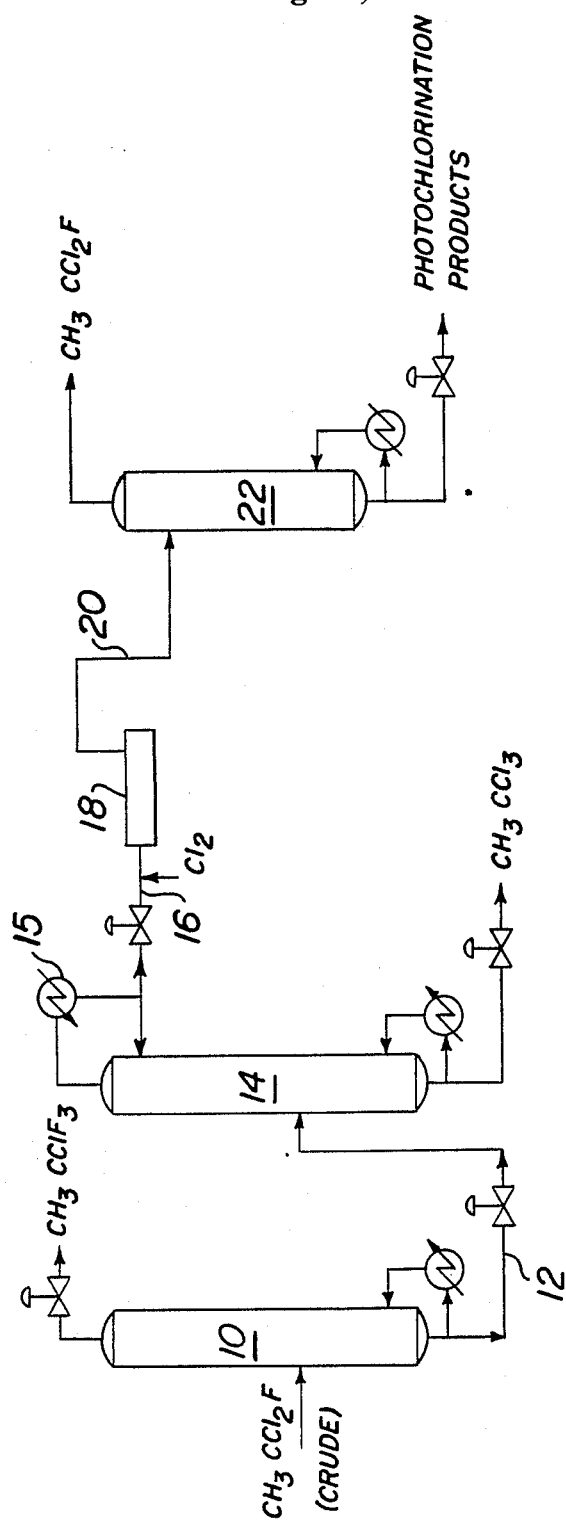

REMOVAL OF UNSATURATED CARBON COMPOUNDS FROM 1,1-DICHLORO-1-FLUOROETHANE

FIELD OF THE INVENTION

The invention relates to the removal of unsaturated carbon compounds from 1,1-dichloro-1-fluoroethane, and in particular relates to the removal of vinylidene chloride from 1,1-dichloro-1-fluoroethane.

BACKGROUND OF THE INVENTION 1,1-Dichloro-1-fluoroethane is presently under consideration as a replacement for trichlorofluoromethane as a foam blowing agent. It has a substantially lower ozone depletion index than trichlorofluoromethane. Moreover, 1,1-dichloro-1-fluoroethane displays a 10-15% greater blowing efficiency in rigid foam, and improved solubility in aromatic polyester polyol, in comparison to trichloro-fluoromethane.

In the manufacture of 1,1-dichloro-1-fluoroethane, by-products are generated which are not easily separated from the desired product by distillation. Various unsaturated carbon compounds, most notably vinylidene chloride, may be produced. Vinylidene chloride is particularly undesirable, since it is a suspected carcinogen. What is needed is a method for removing unsaturated carbon compounds, particularly vinylidene chloride, which may be generated in the production of 1,1-dichloro-1-fluoroethane.

The photochlorination of trichloroethylene and/or tetrachloroethylene is well-known. British Patent No. 591,780; U.S. Pat. No. 2,440,731; Chemical Abstracts 51:16111h (1957), abstracting Ackerman et al., Bull. Soc. Chim. Belges 66, 325–44 (1957); Dainton et al., Trans. Faraday Soc. 53, 460–7 (1957); Chemical Abstracts 53:13748d (1959), abstracting Adam et al., Bull. Soc. Chim. Belges 65, 942–56 (1956); Chemical Abstracts 53:17646 (1959), abstracting Chiltz et al., Bull. Soc. Chim Belges 68, 5–18 (1959); Dusoleil et al., Trans. Faraday Soc. 57, 2197–2209 (1961); Huybrechts et al., Trans. Faraday Soc. 58, 1128–36 (1962); Huybrechts et al., Trans. Faraday Soc. 61(513,pt 9) (1965); LedakoWicz et al., Int. J. Chem. Kinet. 16(4), 345–52 (1984).

Photochlorination of 1,2-dichloroethylene is described in the following: Anderson, Ind. Eng. Chem. 39, 844–46 (1974); Chemical Abstracts 54:5461c (1960), abstracting German Patent No. 967,011; Ayscough et al., Trans. Faraday Soc. 62(7), 1846–58 (1966).

Cocker et al., Trans. Faraday Soc. 58, 284–94 (1962) discloses the photochlorination of cis- and trans-1,2-dichloroethylene, chloroethylene and trichloroethylene.

The photochlorination of vinylidene chloride, cis-and trans-1,2-dichloroethylene, trichloroethylene and tetrachloroethylene is described in Poutsara et al., J. Am. Chem. Soc. 86(18), 3807–14 (1964) and in Beadle et al., J. Chem. Soc., Faraday Trans. 1, 70(8), 1418–33 (1974). The photochlorination of vinylidene chloride is also disclosed in Ayscough et al., Trans. Faraday Soc. 62(7), 1838–45 (1966).

While the gas phase photochlorination of unsaturated carbon compounds is known, the photochlorination reaction has not been heretofore utilized for converting such compounds, in their liquid mixtures with 1,1-dichloro-1-fluoroethane, to higher boiling compounds in order to facilitate separation from 1,1-dichloro-1-fluoroethane.

SUMMARY OF THE INVENTION

A process for removing unsaturated carbon compounds from 1,1-dichloro-1-fluoroethane is provided. A liquid mixture comprising 1,1-dichloro-1-fluoroethane and at least one unsaturated carbon compound is treated with chlorine. The chlorine-treated liquid mixture is irradiated with ultraviolet light to convert at least a portion of the unsaturated carbon compounds in the mixture to photochlorination products. The 1,1-dichloro-1-fluoroethane is thereafter separated from the photochlorination products, such as, for example, by distillation.

The process is particularly useful for separating vinylidene chloride ($CH_2=CCl_2$) from 1,1-dichloro-1-fluoroethane. Vinylidene chloride is photochlorinated to give 1,1,1,2-tetrachloroethane (boiling point=130.5° C.) which is then easily separated from 1-dichloro-1-fluoroethane.

By "unsaturated carbon compound" is meant any organic compound containing at least one double or triple carbon-carbon bond.

BRIEF DESCRIPTION OF THE FIGURE

The Figure is a schematic illustration of an embodiment of the process of the invention.

DETAILED DESCRIPTION OF THE INVENTION

In the manufacture of 1,1-dichloro-1-fluoroethane by the reaction of hydrogen fluoride and 1,1,1-trichloroethane, the latter is susceptible to dehydrohalogination, which leads to the formation of vinylidene chloride and/or other unsaturated by-products. Vinylidene chloride and 1,1-dichloro-1-fluoroethane boil at 37° C. and 32° C., respectively, thus, when one or both are present in very small amounts, they cannot readily be separated by distillation.

The process of the invention provides for the efficient separation of contaminating unsaturated carbon compounds, in particular vinylidene chloride, from 1,1-dichloro-1-fluoroethane. The unsaturated compounds are selectively photochlorinated to form photochlorination products. The latter boil at significantly higher temperatures than 1,1-dichloro-1-fluoroethane, and are therefore readily separated from 1,1-dichloro-1-fluoroethane by a subsequent distillation step.

Unsaturated compounds which may be formed as byproducts with 1,1-dichloro-1-fluoroethane during its preparation from 1,1,1-trichloroethane, include, by way of illustration and not by way of limitation, alkenes and haloalkenes such as vinylidene chloride (b.p. 37° C.), 1,2-dichloroethyle (trans) (b.p. 47.5° C.), 1-chloro-1-fluoroethylene (b.p. −24° C.), and $C_4H_5F_3$, comprising a mixture of 1,1,1-trifluoro-but-2-ene and 1,1,1-trifluorobut-3-ene, and alkynes and haloalkynes such as acetylene, chloroacetylene and dichloroacetylene.

Photochlorination of vinylidene chloride forms 1,1,1,2-tetrachloroethane, which boils at 130.5° C., while 1,2-dichloroethylene (trans) is converted to 1,1,2,2-tetrachloroethane (b.p. 146° C.). Photochlorination of 1-chloro-1-fluoroethylene provides 1,1,2-trichloro-1-fluoroethane (b.p. 88° C.). $C_4H_5F_3$ provides $C_4H_5F_3Cl_2$.

As used herein, by "photochlorination product" is meant the product or products formed by the ultraviolet light-induced chlorination of an unsaturated compound, including, but not necessarily limited to, the photochlorination products identified above. Also included in the definition of "photochlorination products" are the product or products formed by the ultraviolet light-induced chlorination of such saturated compounds which may be contained as contaminants in crude 1,1-dichloro-1-fluoroethane, and which possesses one or more hydrogen atoms susceptible to chlorine substitution. For example, under the herein photochlorination conditions, the saturated hydrofluorocarbon $C_5H_9F_3$ reacts with chlorine to form the photoproduct $C_5H_8F_3Cl$. The latter boils at a temperature higher than 1,1-dichloro-1-fluoroethane, and is therefore readily separated from 1,1-dichloro-1-fluoroethane.

We have found that the photochlorination of any unsaturated halohydrocarbons which may be contained as contaminants in 1,1-dichloro-1-fluoroethane, proceeds preferentially over the reaction of chlorine with 1,1-dichloro-1-fluoroethane. The reaction of chlorine with 1,1-dichloro-1-fluoroethane yields 1,1,2-trichloro-1-fluoroethane. Thus, the invention provides for the selective conversion of the unsaturated contaminants to their corresponding high boiling point photochlorination products without consuming 1,1-dichloro-1-fluoroethane.

The photochlorination procedure may be practiced on any liquid 1,1-dichloro-1-fluoroethane mixture containing unsaturated carbon compounds. The invention is, however, most useful in securing the removal of unsaturated compounds from crude 1,1-dichloro-1-fluoroethane obtained as the product of the hydrofluorination of 1,1,1-trichloroethane with hydrogen fluoride. Such hydrofluorination product mixtures may contain the following, in addition to 1,1-dichloro-1-fluoroethane and unsaturated compounds: minor amounts of the 1,1-dichloro-1-fluoroethane precursor, i.e., 1,1,1-trichloroethane; 1,1,1,3,3-pentafluorobutane, and other saturated $C_4$ compounds, such as, for example, $C_4H_7F_3$; $C_5$ saturated compounds such as, for example, $C_5H_9F_3$; 1-chloro-1,1-difluoroethane; and 1,1,1-tritluoroethane.

It is generally preferred that the amount of 1-chloro-1,1-difluoroethane in the crude 1,1-dichloro-1fluoroethane mixture subject to photochlorination treatment is first reduced to preferably no more than about 100 parts per million, or 0.01% by weight, before photochlorination. This may be accomplished, as described hereinafter, by distilling 1-chloro-1,1-difluoroethane from the crude 1,1-dichloro-1-fluoroethane mixture in advance of photochlorination. It is preferred that the level of 1-chloro-1,1-difluoroethane in the crude 1,1-dichloro-1-fluoroethane liquid is reduced to this level prior to photochlorination, since we have found that, in the presence of excess chlorine, that is, chlorine in excess of the stoichiometric amount necessary to convert the unsaturated carbon compounds present in the mixture to their corresponding photochlorination products, chlorine reacts with 1-chloro-1,1-difluoroethane to form 1,2-dichloro-1,1-difluoroethane (b.p.=46.5° C.). The amount of 1,2-dichloro-1,1-difluoroethane in the final product is kept to a minimum since it is suspected that 1,2-dichloro-1,1-difluoroethane may be carcinogenic. Separation of small amounts of 1,2-dichloro-1,1-difluoroethane (i.e. in the parts per million range) from the final 1,1-dichloro-1-fluoroethane product may be difficult due to the relative proximity of its boiling point (46.5° C.) to the boiling point of 1,1-dichloro-1-fluoroethane (32° C.).

The maximum conversion of 1-chloro-1,1-difluoroethane to 1,2-dichloro-1,1-difluoroethane upon photochlorination under the herein conditions is 10%. Thus, reduction of the 1-chloro-1,1-difluoroethane content of the mixture to no more than 100 parts per million before photochlorination ensures that no more than about 10 parts per million of 1,2-dichloro-1,1-difluoroethane are qenerated upon photochlorination.

Before conducting the photochlorination procedure described in more detail hereinafter, the crude 1,1-dichloro-1-fluoroethane is advantageously separated from contaminating halohydrocarbon compounds, other than unsaturated compounds. Accordingly, halohydrocarbons having boiling points lower than 1,1-dichloro-1-fluoroethane are separated by distilling the crude 1,1-dichloro-1-fluoroethane in a first distillation column under conditions favoring the overhead removal of these lower boiling compounds. Such lower boiling compounds which may be found in the crude 1,1-dichloro-1-fluoroethane include, for example, 1-chloro-1,1-difluoroethane and 1,1,1-trifluoroethane.

The partially purified 1,1-dichloro-1-fluoroethane obtained as a bottom product from the aforesaid first. distillation is thereafter treated to separate the 1,1-dichloro-1-fluoroethane from contaminating hydrohalocarbon compounds having a boiling point higher than 1,1-dichloro-1fluoroethane, e.g., 1,1,1-trichloroethane. Removal is advantageously accomplished by subjecting the partially purified 1,1-dichloro-1-fluoroethane to a second distillation under conditions favoring the removal of 1,1-dichloro-1-fluoroethane as a top product. The higher boiling compounds form the bottom product.

The partially purified 1,1-dichloro-1-fluoroethane top product from the second distillation is condensed, and then treated with chlorine in liquid or vapor form. Preferably, chlorine is added to the 1,1-dichloro-1-fluoroethane condensate as a liquid stream. The amount of chlorine added may vary in an amount up to the solubility limit of chlorine in 1,1-dichloro-1-fluoroethane, at the treatment temperature and pressure. Preferably, 1,1-dichloro-1-fluoroethane is treated in this fashion with from about one to about 3 moles of molecular chlorine per mole of unsaturated carbon compound contained in the liquid subject to chlorination. Most preferably, from about 1 to about 1.5 moles of chlorine per mole of unsaturated carbon compound are utilized.

The addition of chlorine in excess of the stoichiometric requirement ensures conversion of substantially all of the unsaturated compounds contained in the mixture to the corresponding photochlorination products. However, where a chlorine excess is utilized, care should be taken in the first distillation of the crude 1,1-dichloro-1-fluoroethane to ensure removal of contaminating 1-chloro-1,1-difluoroethane to a level of at least as low as 100 parts per million. By doing so, the level of 1,2-dichloro-1,1-difluoroethane in the final purified 1,1-dichloro-1fluoroethane product will be no more than about 10 parts per million. Moreover, we have found that when more than about 3 moles of chlorine per mole of unsaturated carbon compound are utilized, loss of the desired product, 1,1-dichloro-1-fluoroethane, may begin to occur through its conversion to 1,1,2-trichloro-1-fluoroethane (b.p. 88° C.).

The chlorine-treated 1,1-dichloro-1-fluoroethane mixture is thereafter irradiated with ultraviolet light to induce the conversion of the unsaturated contaminants to their corresponding photochlorination products. The irradiation may be conducted in any device or vessel suitable for the ultraviolet irradiation of liquids. According to one construction, the photochlorination device comprises an approximately 3¼ inch outside diameter quartz tube, approximately six to seven feet long. The quartz tube is coaxially inserted into a stainless steel conduit having an inside diameter of about 4 inches, or approximately ¾ inch larger than the quartz tube outer diameter. The liquid subject to irradiation is pumped through the annular space between the quartz tube and the steel conduit, which serves as an irradiation zone. The light source is advantageously contained within the core of the quartz tube.

The energy output required to trigger the chlorination reaction is generally inversely proportional to the reaction time. Thus, when higher output radiation sources are utilized, less time is required for the chlorination reaction to proceed to completion. The amount of energy actually applied to the chlorine-treated 1,1-dichloro-1fluoroethane mixture can vary over a wide range. Where the molar ratio of molecular chlorine to unsaturated compound in the feed to the irradiation zone is from about 1:1 to about 3:1, the mixture is advantageously irradiated with ultraviolet light at a rate from about 1,000 watt-hours per kilogram of the mixture subject to irradiation, to about 3,000 watt-hours per kilogram. Where the chlorine:unsaturated compound ratio in the mixture is about 1:1, the amount of radiation applied is preferably from about 2,000 to about 3,000 watt-hours/kg. Likewise, where the chlorine:unsaturated compound ratio is about 3:1, the amount of irradiation applied is preferably from about 1,000 watt-hours/kg to about 1,500 watt-hours/kg.

The temperature in the irradiation zone may vary over a considerable range, from the freezing point of 1,1-dichloro-1-fluoroethane ($-103°$ C.) up to its boiling point at the operating pressure. The preferred operating temperature is from about 20° C. to about 60° C., so that the heating and cooling expenses are minimized, and the vapor pressure; of the 1,1-dichloro-1-fluoroethane subject to treatment is at or near atmospheric pressure.

1,1-Dichloro-1-fluoroethane is thereafter separated from the photochlorination products which were formed by the aforesaid photochlorination treatment. Separation is most advantageously achieved by distillating the photochlorinated liquid and removing therefrom substantially pure 1,1-dichloro-1-fluoroethane as the distillation overhead product. The photochlorination products, which boil at appreciably higher temperatures than 1,1-dichloro-1-fluoroethane, form the distillation bottom product.

The practice of the invention is illustrated by the following non-limiting examples.

EXAMPLE 1

Crude 1,1-dichloro-1-fluoroethane was photochlorinated under various conditions to determine the effects of chlorine concentration, reaction time (i.e., duration of U.V. irradiation) and temperature on unsaturated impurities, and on the production of new impurities.

The crude 1,1-dichloro-1-fluoroethane was divided into 21 samples. Each sample was placed in a quartz tube and sealed with a septum so that it could be analyzed by gas chromatography without opening. All the sample bottles were kept in a light-tight wrapper, except when irradiated. The ultraviolet source utilized was a 450-watt mercury argon lamp placed inside a black box. The light was turned on and allowed to warm before initiating the photochlorination reactions. The tube was removed from its wrapper in a dark room and inserted through a hole in the box for the desired reaction time. The tube was thereafter removed from the box, wrapped and placed in ice to prevent any further photochlorination reaction. The reaction time was increased inversely proportional to the wattage of the light source to maintain total energy input at a constant value. The experimental design comprised a two factor Box-Wilson design in chlorine concentration and reaction time. To measure the effect of temperature, the samples were irradiated at two different temperatures, producing two parallel Box-Wilson designs. Following photochlorination, the samples were analyzed by gas chromatography. The results from the chromatography were analyzed using a RS/1 statistical program. Those results are summarized in Table 1.

The crude 1,1-dichloro-1-fluoroethane liquid (untreated, Table 1) had the following composition, by weight%, before treatment:

| A | 1-chloro-1,1-difluoroethane | 0.030 |
| --- | --- | --- |
| B | $C_4H_5F_3$ | 0.003 |
| C | $C_4H_7F_3$ | 0.003 |
| D | 1,1,1,3,3-PENTAFLUORO-BUTANE | 0.614 |
| E | $C_5H_9F_3$ | 0.026 |
| F | 1,1-dichloro-1-fluoroethane | 99.193 |
| G | vinylidene chloride | 0.125 |
| H | 1,1,1-trichloroethane | 0.004 |
| I | Other (high boiling) | 0.002 |

The following impurities were generated upon photochlorination, in the amounts set forth in Table 1:

| J | 1,2-dichloro-1,1-difluoroethane |
| --- | --- |
| K | Unknown (30.3 g.c. retention time) |
| L | 1,1,2-trichloro-1-fluoroethane |
| M | 1,1,1,2-tetrachloroethane |

Those components represented by their empirical formulas are deemed to include isomers of the same formula. For example, $C_4H_5F_3$ includes the isomers 1,1,1-trifluorobut-2-ene and 1,1,1-trifluorobut-3-ene.

TABLE 1

| Expt. No. | Photochlorination Conditions | | | Product Analysis (wt %) | | | | | | | | | | | | |
| --- | --- | --- | --- | --- | --- | --- | --- | --- | --- | --- | --- | --- | --- | --- | --- | --- |
| | wt % Cl$_2$ | Irrad. Time | T (°C.) | A | B | C | D | E | F | G | H | I | J | K | L | M |
| Untreated | 0 | 0 | 0 | .030 | .003 | .003 | .614 | .026 | 99.193 | .125 | .004 | .002 | N.D. | N.D. | N.D. | N.D. |
| 1 | 0 | 150 | 0 | .033 | .002 | .002 | .599 | .023 | 99.231 | .100 | .004 | .001 | .0008 | .001 | N.D. | .001 |
| 2 | 0 | 150 | 21 | .030 | .002 | .003 | .602 | .015 | 99.230 | .102 | .004 | .001 | N.D. | N.D. | N.D. | N.D. |
| 3 | .088 | 44 | 0 | .030 | N.D. | .002 | .590 | .019 | 99.230 | .067 | .004 | .005 | N.D. | .002 | .004 | .046 |

TABLE 1-continued

| Expt. No. | Photochlorination Conditions | | | Product Analysis (wt %) | | | | | | | | | | | | |
|---|---|---|---|---|---|---|---|---|---|---|---|---|---|---|---|---|
| | wt % Cl₂ | Irrad. Time | T (°C.) | A | B | C | D | E | F | G | H | I | J | K | L | M |
| 4 | .088 | 44 | 21 | .029 | .002 | .002 | .596 | .021 | 99.214 | .074 | .004 | .004 | N.D. | .002 | .005 | .048 |
| 5 | .088 | 256 | 0 | .033 | N.D. | .002 | .595 | .019 | 99.252 | .048 | .004 | .007 | N.D. | .003 | .005 | .033 |
| 6 | .088 | 256 | 21 | .030 | N.D. | .002 | .588 | .019 | 99.235 | .040 | .004 | .005 | N.D. | .003 | .006 | .067 |
| 7 | .300 | 0 | 0 | .028 | .002 | .002 | .577 | .025 | 99.245 | .117 | .004 | N.D. | N.D. | N.D. | N.D. | N.D. |
| 8 | .300 | 0 | 21 | .026 | .002 | .003 | .572 | .025 | 99.250 | .117 | .004 | N.D. | N.D. | N.D. | N.D. | N.D. |
| 9 | .300 | 150 | 0 | .029 | N.D. | .002 | .573 | .011 | 99.234 | .013 | .004 | .012 | N.D. | .005 | .015 | .103 |
| 10 | .300 | 150 | 0 | .030 | N.D. | .002 | .585 | .013 | 99.228 | .020 | .004 | .015 | .0009 | .005 | .012 | .086 |
| 11 | .300 | 150 | 21 | .027 | N.D. | .003 | .572 | .008 | 99.175 | N.D. | .004 | .015 | N.D. | .006 | .026 | .160 |
| 12 | .300 | 150 | 21 | .028 | N.D. | .003 | .580 | .002 | 99.100 | N.D. | .004 | .028 | N.D. | .008 | .058 | .187 |
| 13 | .300 | 300 | 0 | .033 | N.D. | .002 | .580 | .014 | 99.245 | .015 | .004 | .012 | .001 | .005 | .010 | .079 |
| 14 | .300 | 300 | 21 | .032 | N.D. | .005 | .587 | N.D. | 99.023 | N.D. | .004 | .049 | .003 | .010 | .126 | .165 |
| 15 | .512 | 44 | 0 | .027 | N.D. | .002 | .561 | .010 | 99.226 | .014 | .004 | .023 | .0007 | .006 | .017 | .111 |
| 16 | .512 | 44 | 21 | .027 | N.D. | .002 | .563 | N.D. | 98.849 | N.D. | .004 | .039 | N.D. | .004 | .344 | .168 |
| 17 | .512 | 256 | 0 | .029 | N.D. | .002 | .562 | .012 | 99.230 | .012 | .004 | .031 | .0009 | .006 | .016 | .096 |
| 18 | .512 | 256 | 21 | .026 | N.D. | .004 | .560 | N.D. | 98.710 | N.D. | .004 | .056 | N.D. | .005 | .458 | .177 |
| 19 | .600 | 150 | 0 | .028 | N.D. | .002 | .557 | .012 | 99.248 | .015 | .004 | .025 | .001 | .005 | .015 | .087 |
| 20 | .600 | 150 | 21 | .025 | N.D. | .004 | .550 | N.D. | 98.464 | N.D. | .004 | .056 | N.D. | .003 | .718 | .176 |

N.D. = not detected

As is observed from a consideration of Table 2, no photochlorination occurs in the absence of irradiation (Experiments 7 and 8). Likewise, there was very little reaction in the absence of chlorine (Experiments 1 and 2). 1,1,1-Trichloroethane (H) did not react in any of the experiments.

An unknown with the gas chromatograph retention time of 30.3 minutes (K) was produced by the photochlorination process. The concentration of the unknown was observed to increase with increasing chlorine concentrations and reaction times. The concentration of 1,1,1,2-tetrachloroethane (L), another photochlorination product, was observed to increase with chlorine concentration.

Experiments 5 and 6 show that at a Cl₂:unsaturated compound ratio of 0.98:1 (corresponding to addition of 0.088 wt.% Cl₂), vinylidene chloride concentration (G) is reduced 65% by the photochlorination treatment, while $C_4H_5F_3$ (B) is reduced to below the detection limits of the analysis (7 ppm). Experiments 11, 12 and 14 show that at a Cl₂:unsaturated compound ratio of 3.2:1 (corresponding to addition of 0.300 wt.% Cl₂), vinylidene chloride (G) and $C_4H_5F_3$ (B) are both reduced to below 10 parts per million. The production of the vinylidene chloride photoproduct 1,1,1,2-tetrachloroethane (M) increased with chlorine concentration and reaction time. The high boiling unknowns (I) initially present in the mixture were also observed to increase with increasing chlorine concentration and reaction time.

It should be noted that conversion of 1,1-dichloro-1-fluoroethane (F) was very small, with the maximum loss of 1,1-dichloro-1-fluoroethane taking place at the highest chlorine concentrations, reaction temperatures and reaction times (Experiment Nos. 16, 18 and 20).

1-Chloro-1,1-difluoroethane (A) concentration was reduced at higher chlorine concentrations, but was increased at longer reaction times. The maximum conversion of 1-chloro-1,1-difluoroethane to 1,2-dichloro-1,1-difluoroethane was 10% (Experiment 14).

The concentration of $C_4H_7F_3$ (C) was reduced in some experiments, but the concentration was too small to adequately correlate the results. Thus, it is believed that $C_4H_7F_3$ does not react with chlorine under the conditions of the Example. On the other hand, $C_5H_9F_3$ (E) reacts with chlorine to yield the substitution product $C_5H_8F_3Cl$. The latter may be separated from 1,1-dichloro-1-fluoroethane by distillation. Significantly, the concentrations of the olefins vinylidene chloride (G) and $C_4H_5F_3$ (B) were reduced by increasing chlorine concentration and increasing photochlorination reaction time.

The process of the present invention is useful for removing acetylenic as well as olefinic compounds from 1,1-dichloro-1-fluoroethane. The reaction products of the photochlorination of acetylenic compounds boil at temperatures higher than the boiling point of 1,1-dichloro-1fluoroethane, and may therefore be readily separated from 1,1-dichloro-1-fluoroethane by distillation.

EXAMPLE 2

A vial containing approximately 50cc of 1,1-dichloro-1-fluoroethane was treated with acetylene in an amount such that the resulting solution contained approximately 0.20 wt.% acetylene. Chlorine in excess of the amount required to fully chlorinate the acetylene was added to the solution, which was then exposed to sunlight as a source of ultraviolet light. When the solution cleared from the color of the dissolved chlorine, it was analyzed for acetylene content. No acetylene was detected. The photochlorination product was 1,1,2,2-Tetrachloroethane, b.p. 146° C.

A system for the practice of the present invention is illustrated in more detail in the Figure. A stream of crude 1,1-dichloro-1-fluoroethane, such as from the hydrofluoroination 1,1,1-trichloroethane, is subject to distillation in column 10. Column 10 is operated, for example, at a temperature at the column top of about 77° C. and a temperature at the column bottom of about 88° C., and a pressure of about 40 PSIG. The overhead product of column 10 comprises halohydrocarbons having a lower boiling point than the boiling point of 1,1-dichloro-1-fluoroethane. 1-Chloro-1,1-difluoroethane is the predominant lower boiling compound obtained in the overhead product. The bottom product of distillation column 10 comprises partially purified 1,1-dichloro-1-fluoroethane from which the lower boiling compounds have been separated. The bottom product is pumped through line 12 to distillation column 14, which is operated, for example, at a temperature at the column top of about 49° C. and a temperature at the column bottom of about 60° C., and a pressure of about 10 PSIG. The bottom product comprises halohydrocarbons, most notably 1,1,1-trichloroethane, which have a boiling point higher than that of 1,1-dichloro-1-fluoroethane. The overhead product of column 14 comprises the further purified 1,1-dichloro-1-fluoroethane which is condensed by condenser 15 to a stream in line 16. The partially purified 1,1-dichloro-1-fluoroethane liquid stream is combined with chlorine and then irradiated with ultraviolet light in photochlorinator 18. The flowrate through the photochlorinator is, for example, 60 lbs per minute, with an ultraviolet lamp source intensity of, for example, 7500 watts, and a residence time of liquid in the photochlorinator of, for example, 12 seconds. The inlet temperature of the material in the photochlorinator is, for example, in the range of about 4° C. to about 15° C., with the outlet temperature ranging from about 40° C. to about 50° C. The increase in temperature is due primarily from the radiant heat transfer from the ultraviolet light source.

Following photochlorination, the partially purified 1,1-dichloro-1-fluoroethane stream may be optionally treated to remove any residual chlorine, HCl and acidic fluorides (presumably hydrogen fluoride) generated in the photochlorination process. We have, for the most part, been unable to detect any residual chlorine in the 1,1-dichloro-1-fluoroethane stream following photochlorination. However, if present, residual chlorine may be removed, for example, by passing the partially purified 1,1-dichloro-1-fluoroethane over a bed of activated carbon (not shown). Water which may have been produced in the process, and any hydrogen fluoride which may have formed, may be removed by passing the product through a bed of activated alumina (not shown). HCl is removed, for example, by distillation, or by means of a potassium hydroxide column (not shown). The potassium hydroxide column may also be utilized to remove acidic fluorides. The construction and operation of such absorption devices is well known to those skilled in the art.

The photochlorinator product is taken through line 20 to yet another distillation column 22 wherein 1,1-dichloro-1-fluoroethane is distilled off as an overhead product. Distillation column 22 is similar to distillation column 14 and is operated, for example, at the same temperature and pressure as column 14. The photochlorination products, which have a boiling point higher than the boiling point of 1,1-dichloro-1-fluoroethane, are taken as the bottom product of column 22.

The conditions in the foregoing description of the Figure are for illustration only, and should not be construed as limiting the scope of the invention.

The present invention may be embodied in other specific forms without departing from the spirit or essential attributes thereof and, accordingly, reference should be made to the appended claims, rather than to the forgoing specification, as indicating the scope of the invention.

We claim:

1. A process for removing unsaturated carbon compounds from 1,1-dichloro-1-fluoroethane comprising:
    treating a liquid mixture comprising 1,1-dichloro-1-fluoroethane and at least one unsaturated carbon compound with chlorine;
    irradiating said chlorine-treated liquid mixture with ultraviolet light to selectively convert at least a portion of the unsaturated carbon compounds in the mixture to photochlorination products thereof no or small consumption of 1,1-dichloro-1-fluoroethane; and
    separating 1,1-dichloro-1-fluoroethane from said photochlorination products.

2. A process according to claim 1 wherein the step of separating 1,1-dichloro-fluoroethane from the photochlorination products comprises distilling 1,1-dichloro-1-fluoroethane from the liquid mixture.

3. A process according to claim 2 wherein the mixture subject to treatment contains at least one halohydrocarbon compound having a lower boiling point than 1,1-dichloro-1fluoroethane, and at least a portion of said lower boiling compound is separated from the liquid mixture prior to chlorine treatment.

4. A process according to claim 3 wherein the mixture subject to treatment contains at least one halohydrocarbon compound having a higher boiling point than 1,1-dichloro-1-fluoroethane, and at least a portion of said higher boiling compound is separated from the liquid mixture prior to chlorine treatment.

5. A process according to claim 3 wherein the lower boiling compound separated from the mixture comprises 1-chloro-1,1-difluoroethane, and the amount of 1-chloro-1,1-difluoroethane in the liquid mixture is thereby reduced to no more than about 100 parts per million parts of the mixture, by weight.

6. A process according to claim 2 wherein the liquid mixture is treated with from about 1 to about 3 moles of molecular chlorine per mole of unsaturated carbon compound contained in the mixture.

7. A process according to claim 6 wherein the liquid mixture is treated with from about 1 to about 1.5 moles of molecular chlorine per mole of unsaturated carbon compound contained in the mixture.

8. A process according to claim 7 wherein the liquid mixture is irradiated with ultraviolet light at a rate from about 1000 watt-hours to about 3000 watt-hours, per kilogram of the mixture.

9. A process according to claim 2 further comprising the additional step of removing HCl and residual chlorine from 1,1-dichloro-1-fluoroethane following its separation from the photochlorination products.

10. A process according to claim 2 wherein the unsaturated carbon compounds removed from the liquid mixture subject to treatment include vinylidene chloride.

11. A process for separating 1,1-dichloro-1-fluoroethane from its mixtures with unsaturated carbon compounds comprising:
    (a) distilling from said mixture halohydrocarbons contained therein having a boiling point lower than the boiling point of 1,1-dichloro-1-fluoroethane;
    (b) distilling 1,1-dichloro-1-fluoroethane from the bottom product of (a) to separate said 1,1-dichloro-1-fluoroethane from halohydrocarbons contained in said mixture having a boiling point higher than the boiling point of 1,1-dichloro-1-fluoroethane;
    (c) condensing the distillate from (b) to form a liquid distillate comprising 1,1-dichloro-1-fluoroethane;
    (d) treating the liquid distillate from (c) with chlorine in the amount of from about 1 mole to about 3 moles of molecular chlorine, per mole of unsaturated carbon compound in the liquid distillate;
    (e) irradiating the chlorine-treated liquid with ultraviolet light to selectively convert at least a portion of the unsaturated carbon compounds contained therein to photochlorination products with no or small consumption of 1,1-dichloro-1-fluoroethane; and (f) separating 1,1-dichloro-1-fluoroethane from said photochlorination products by distilling 1,1-dichloro-1-fluoroethane from the irradiated liquid.

12. A process according to claim 11 wherein the mixture subject to treatment includes vinylidene chloride.

13. A process according to claim 11 wherein the liquid distillate from (c) is treated with chlorine in the amount of from about 1 mole to about 1.5 moles of molecular chlorine, per mole of unsaturated carbon compound in the liquid distillate.

* * * * *

UNITED STATES PATENT AND TRADEMARK OFFICE
CERTIFICATE OF CORRECTION

PATENT NO. : 4,948,479
DATED : August 14, 1990
INVENTOR(S) : Wayne E. Brooks, et al.

It is certified that error appears in the above-identified patent and that said Letters Patent is hereby corrected as shown below:

Column 1, line 21, change "trichloro-fluoromethane" to --trichlorofluoromethane--; Column 1, line 44, change "LedakoWicz" to --Ledakowicz--; Column 2, lines 20 - 21, change "1-dichloro-1-fluoroethane" to --1,1-dichloro-1-fluoroethane--; Column 2, line 55, change "1,2-dichloroethyle" to --1,2-dichloroethylene--; Column 3, line 43, change "1,1,1-tritluoroethane" to --1,1,1-trifluoroethane--; Column 3, lines 45-46, change "1,1-dichloro-1fluoroethane" to --1,1-dichloro-1-fluoroethane--; Column 4, line 10, change "qenerated" to --generated--; Column 4, line 25, omit "." at end of line; Column 4, lines 29 and 60, change "1,1-dichloro-1fluoroethane" to --1,1-dichloro-1-fluoroethane--; Column 5, line 42, omit ";" after "pressure"; Column 8, lines 31-32, change "1,1-dichloro-1fluoroethane" to --1,1-dichloro-1-fluoroethane--; Column 8, line 51, change "hydrofluoroination" to --hydrofluorination--. Claim 1, line 10, insert --with-- before "no"; Claim 3, line 4, change "1,1-dichloro-1fluoroethane" to --1,1-dichloro-1-fluoroethane--. In the drawing, change "$CH_3CClF_3$" to --$CH_3CClF_2$--.

Signed and Sealed this

Fifth Day of January, 1993

Attest:

DOUGLAS B. COMER

Attesting Officer

Acting Commissioner of Patents and Trademarks